United States Patent
Aldridge et al.

(10) Patent No.: US 10,064,677 B2
(45) Date of Patent: Sep. 4, 2018

(54) DRIVE SCREW BAILOUT FOR MOTORIZED RF DEVICE

(71) Applicant: Ethicon Endo-Surgery, LLC, Guaynabo, PR (US)

(72) Inventors: Jeffrey L. Aldridge, Lebanon, OH (US); Jason R. Lesko, Cincinnati, OH (US); Geoffrey S. Strobl, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 270 days.

(21) Appl. No.: 14/940,439

(22) Filed: Nov. 13, 2015

(65) Prior Publication Data

US 2017/0135748 A1    May 18, 2017

(51) Int. Cl.
| | |
|---|---|
| *A61B 17/32* | (2006.01) |
| *A61B 18/14* | (2006.01) |
| *F16H 25/20* | (2006.01) |
| *A61B 18/00* | (2006.01) |

(52) U.S. Cl.
CPC ..... *A61B 18/1445* (2013.01); *F16H 25/2025* (2013.01); *A61B 2018/0063* (2013.01); *A61B 2018/1455* (2013.01); *F16H 2025/209* (2013.01)

(58) Field of Classification Search
CPC ............ A61B 17/32; A61B 17/320016; A61B 17/32002; A61B 2017/320028; A61B 2017/320073; A61F 9/00763

USPC .......................... 606/167, 170, 171, 173, 177
See application file for complete search history.

(56) References Cited

U.S. PATENT DOCUMENTS

| | | | |
|---|---|---|---|
| 2009/0202387 A1 | 8/2009 | Dlugos, Jr. et al. | |
| 2010/0089970 A1* | 4/2010 | Smith ............. | A61B 17/07207 |
| | | | 606/170 |

* cited by examiner

*Primary Examiner* — Melanie Tyson
(74) *Attorney, Agent, or Firm* — Mintz Levin Cohn Ferris Glovsky and Popeo, P.C.

(57) ABSTRACT

Methods and devices are provided for retracting a cutting assembly in the event of a failure on a motorized electrosurgical device. As an example, a surgical device is provided that includes a handle portion with an elongate shaft extending distally that has first and second jaws configured to engage tissue therebetween. A cutting assembly cuts tissue engaged between the first and second jaws. A drive shaft extends from the handle through the elongate shaft and moves the cutting assembly. A motorized gear assembly moves the drive shaft. The drive shaft is movable between a first position in which the drive shaft is engaged with the motorized gear assembly such that actuation of the motorized gear assembly drives the drive shaft, and a second position in which the drive shaft is disengaged from the motorized gear assembly such that the drive shaft can move independent of the gear assembly.

14 Claims, 5 Drawing Sheets

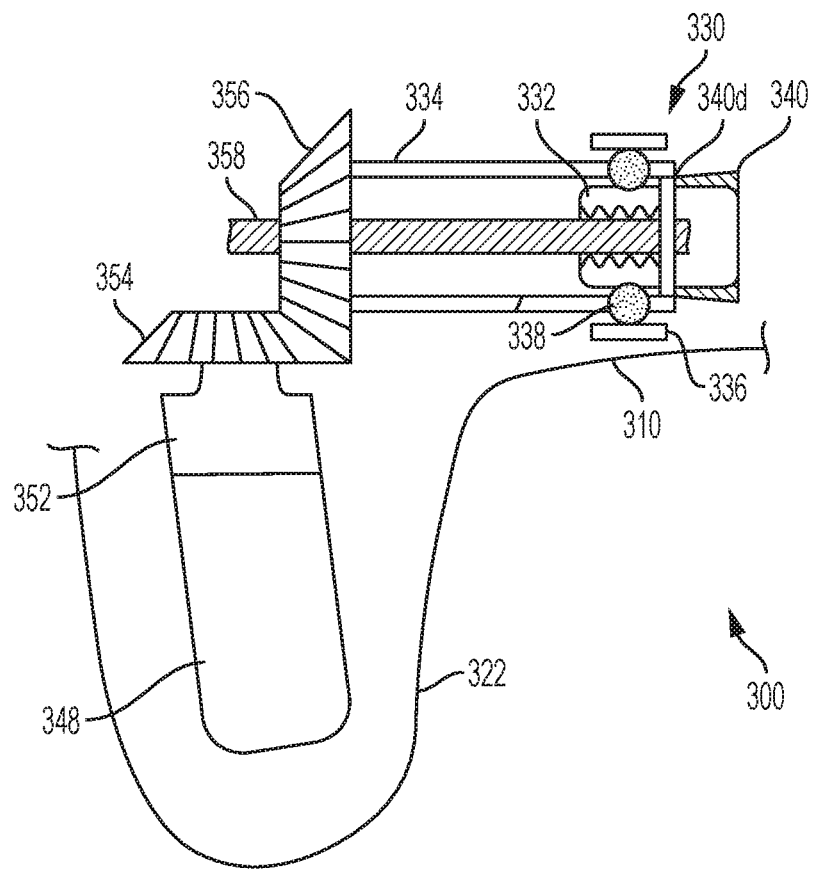
FIG. 5
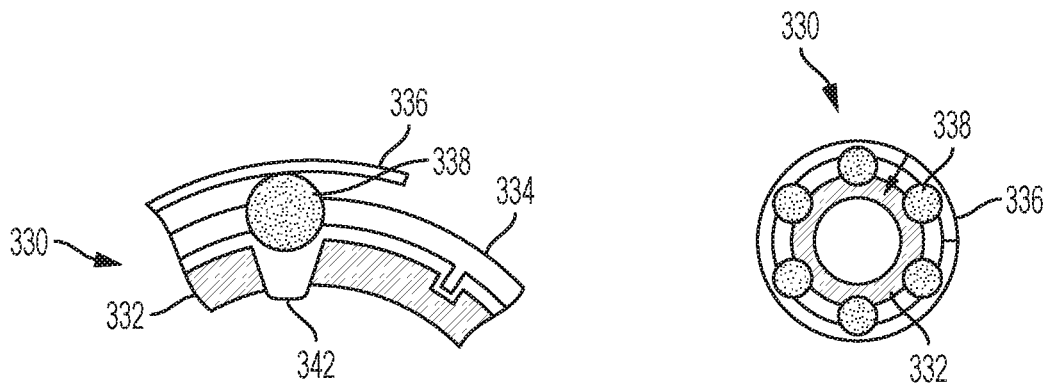
FIG. 6
FIG. 7

DRIVE SCREW BAILOUT FOR MOTORIZED RF DEVICE

FIELD

Methods and devices are provided for retracting a cutting assembly in the event of a failure on a motorized electrosurgical device.

BACKGROUND

Endoscopic surgical instruments are often preferred over traditional open surgical devices since a smaller incision associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, stapler, clip applier, access device, drug/gene therapy delivery device, and energy device using ultrasound, RF, laser, etc.).

Endoscopic devices are passed through an access port, such as a trocar, to allow the distal end effector to engage tissue within a body cavity of a patient. With powered devices, any problems that occur may prevent removal of the device through the access port. For example, in the event the end effector becomes jammed during a firing stroke or the device otherwise fails, the end effector cannot be removed because tissue is engaged between the jaws. The surgeon may be forced to open up the patient and cut the instrument out of the patient, potentially causing serious harm to the patient.

Accordingly, there remains a need for methods and devices for retracting a cutting assembly in the event of a failure on a motorized electrosurgical device.

SUMMARY

Various methods and devices are provided for retracting a cutting assembly in the event of a failure on a motorized electrosurgical device.

In one aspect, a surgical device is provided that includes a handle portion, a cutting assembly, a drive shaft, and a motorized gear assembly. The handle portion has an elongate shaft extending distally therefrom with first and second jaws at a distal end thereof that are configured to engage tissue therebetween. The cutting assembly is configured to move relative to the first and second jaws so as to cut tissue engaged between the first and second jaws. The drive shaft extends from the handle through the elongate shaft and is coupled to the cutting assembly for moving the cutting assembly relative to the first and second jaws, and the motorized gear assembly is coupled to the drive shaft and is configured to cause movement of the drive shaft. The drive shaft is movable between a first position in which the drive shaft is operatively engaged with the motorized gear assembly such that actuation of the motorized gear assembly drives the drive shaft, and a second position in which the drive shaft is operatively disengaged from the motorized gear assembly such that the drive shaft can move independent of the gear assembly.

The surgical device can vary in any number of ways. For example, the drive shaft can be operatively engaged to the motorized gear assembly by a nut and ball bearing assembly. As another example, the handle portion can include a lever configured to open and close the jaws and that is configured to operatively disengage the drive shaft from the motor and to move the drive shaft proximally to retract the cutting assembly. The lever can also include a plurality of gears engageable with the drive shaft. As another example, a removable pin can bias a plurality of balls to operably couple the drive shaft to the motorized gear assembly, and proximal movement of the pin can cause the balls to disengage the drive shaft from the motorized gear assembly. In another example, a plurality of balls can operatively engage the drive shaft to the motorized gear assembly, and a wedge can be configured to be moved distally to cause the balls to operatively disengage the drive shaft from the motorized gear assembly.

In another aspect, a surgical device is provided that includes a handle, a cutting assembly, a drive shaft, and a motor. The handle has an elongate body extending distally therefrom and has first and second jaws on the distal end of the elongate body. The cutting assembly is configured to move relative to the first and second jaws so as to cut tissue engaged between the first and second jaws, and the drive shaft extends through the elongate shaft. The cutting assembly is coupled to the cutting assembly for moving the cutting assembly relative to the first and second jaws, and the drive shaft is operably coupled to a motor by a ball and detent assembly. The ball and detent assembly are releasable to disengage the drive shaft from the motor.

The surgical device can vary in any number of ways. For example, a cone can be distally advanceable along the drive shaft to release the ball and detent assembly. As another example, the handle can include a lever configured to release the ball and detent assembly to disengage the drive shaft from the motor. The lever can include a plurality of gears engageable with the drive shaft. The lever can overcome a spring bias to release the ball and detent assembly. As another example, a removable pin can bias the ball and detent assembly to operatively couple the drive shaft to the motor, and proximal movement of the pin can cause the ball and detent assembly to operatively disengage the drive shaft from the motor.

In another aspect, a method is provided for cutting tissue that includes engaging tissue between first and second jaws on a surgical device. The method also includes actuating the surgical device to cause power to be delivered to a motor such that the motor drives a gear assembly that advances a drive shaft to advance a cutting assembly along the first and second jaws to cut the tissue engaged between the first and second jaws. The method also includes actuating a bailout mechanism to operatively disengage the drive shaft from the motorized gear assembly, and manually driving the drive shaft to move the cutting assembly along the first and second jaws.

The method can vary in any number of ways. For example, a ball and detent assembly can become disengaged when the bailout mechanism is activated. As another example, the method can include advancing a cone distally to disengage the ball and detent assembly. As still another example, the method can include withdrawing a pin proximally to disengage the ball and detent assembly. As yet another example, after the drive shaft has been disengaged, the method can include moving a closure trigger on the surgical device away from a stationary handle to move the drive shaft proximally.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 5 is a partial side cross-sectional view of another embodiment of a powered surgical device;

FIG. 6 is a partial cross-sectional view of the bailout mechanism of FIG. 5;

FIG. 7 is a cross-sectional view of the bailout mechanism of FIG. 5;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for retracting a cutting assembly in the event of a failure on a motorized electrosurgical device. In particular, methods and devices are provided for disengaging a drive shaft on a motorized electrosurgical device.

Figure 1:
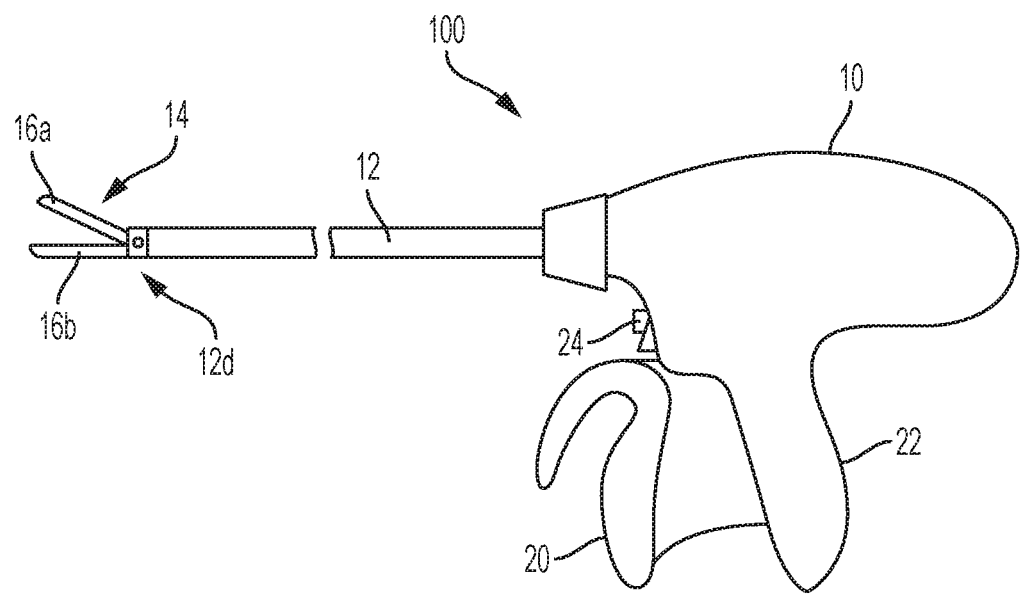
FIG. 1 is a side view illustration of one embodiment of a powered surgical device.

FIG. 1 illustrates one embodiment of a surgical device configured to grasp and cut tissue. As shown, the illustrated surgical device 100 generally includes a proximal handle portion 10, a shaft portion 12, and an end effector 14 for grasping tissue. The proximal handle portion 10 can be any type of pistol-grip, scissor grip, pencil-grip, or other type of handle known in the art that is configured to carry various actuators, such as actuator levers, knobs, triggers, or sliders, for actuating various functions such as rotating, articulating, approximating, and/or firing the end effector 14. In the illustrated embodiment, the proximal handle portion 10 includes a stationary grip 22 and a closure grip 20 that is movable toward and away from the stationary grip 22 to open and close jaws of the end effector 14. The shaft portion 12 extends distally from the proximal handle portion and has a lumen (not shown) extending therethrough for carrying mechanisms for actuating the end effector 14.

The end effector can have a variety of sizes, shapes, and configurations. As shown in FIG. 1, the end effector 14 includes a first upper jaw 16a and a second lower jaw 16b disposed at a distal end 12d of the shaft portion 12. The jaws 16a, 16b are moveable between an open position in which the jaws 16a, 16b are spaced a distance apart, and a closed position in which the jaws 16a, 16b are moved toward one another and are substantially opposed. When the jaws 16a, 16b are in the closed position, a longitudinal axis of the upper jaw 16a can be substantially parallel to a longitudinal axis of the lower jaw 16b and the jaws 16a, 16b can be in direct contact for engaging tissue therebetween. In the illustrated embodiment, the upper jaw 16a pivots relative to the shaft portion 12 and relative to the lower jaw 16b while the lower jaw 16b remains stationary. While the illustrated jaws 16a, 16b have a substantially elongate and straight shape, a person skilled in the art will appreciate that one or both of the jaws 16a, 16b can be in various directions. The jaws 16a, 16b can have any suitable axial length for engaging tissue, and the length can be selected based on the targeted anatomical structure for transection and/or sealing.

As indicated above, the surgical device 100 can have a closure actuator that can be configured to open and close the jaws 16a, 16b of the end effector 14. Manipulation of the closure actuator can pivot or otherwise move the jaws relative to one another such that the jaws can engage tissue, move anatomical structures, or perform other surgical functions. The closure actuator can have various sizes, shapes, and configurations, but in the illustrated embodiment the closure actuator includes the closure grip 20 and the stationary grip 22. The closure grip 20 can be moveable toward and away from stationary grip 22, such as via pivoting. In particular, the closure grip 20 can have a first position in which it is angularly offset and spaced apart from the stationary grip 22 and the jaws 16a, 16b of the end effector 14 are open. The closure grip 20 can have a second position where it is positioned adjacent to, or substantially in contact with, the stationary grip 22 and the jaws 16a, 16b of the end effector 14 can engage tissue and apply a force to tissue disposed therebetween. The closure grip 20 can be biased to the first open position with the jaws 16a, 16b of the end effector 14 being open, as shown in FIG. 1. The closure grip 20 can move the jaws 16a, 16b between the open and closed positions using manual or powered components. For example, in manually actuated embodiments, the closure grip 20 can be coupled to gears that interact with a rack disposed within the handle. Manual movement of the closure grip 20 toward the stationary grip 22 can move the rack either proximally or distally relative to the end effector 14 to either pull or push the jaws 16a, 16b closed. In other embodiments, the drive shaft can include or be coupled to a drive screw which can be moved proximally by a drive nut that is rotated by a series of gears. In powered embodiments, a motor can be disposed in the proximal handle portion 10 and manual movement of the closure grip 20 can cause a control signal to be sent to the motor, which can interact with various gears or other components to cause the jaws 16a, 16b to close. The closure grip 20 can interact with one or more locking features (not shown) configured to lock the closure grip 20 relative to the stationary handle 22. For example, the locking feature can automatically engage when the closure grip 20 substantially contacts the stationary handle 22 or the locking feature can automatically engage at each position the closure grip 20 is pivoted through, such as via ratcheting.

In certain embodiments the surgical device can also have a second actuator, such as actuator 24, that can be separate from the closure actuator 20. The second actuator can be configured to advance a cutting assembly, apply energy to tissue, or both, and is referred to herein as a "firing actuator." The firing actuator 24 can have various sizes, shapes, and configurations, but in the illustrated embodiment it is in the form of a button or trigger that can be depressed by a user. In another embodiment, the firing actuator 24 can be in the form of a switch, lever, etc., that can be slid, pivoted, or otherwise moved by a user. Depressing or pivoting the actuator can activate various elements in the device, and can cause a cutting assembly to advance through the end effector and/or cause energy to be delivered to the jaws. For example, depressing or pivoting the firing actuator can cause a cutting assembly to advance distally and/or retract proximally relative to the jaws 16a, 16b. More specifically, the firing actuator can be in electrical communication with a motor disposed in the proximal handle portion 10. The motor can be operatively coupled to the cutting assembly using known components, such as one or more gears and a rack or drive screw.

Figure 2:
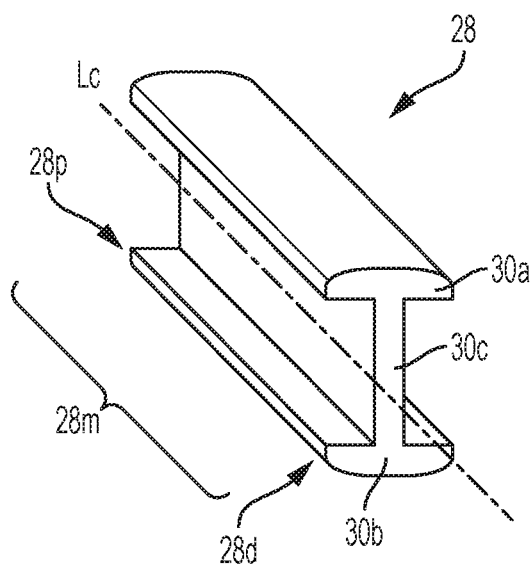
FIG. 2 is a perspective view illustration of a compression member of the powered surgical device of FIG. 1.

The cutting assembly can be configured to transect tissue captured between the jaws, and it can be sized and shaped to transect or cut various thicknesses and types of tissue. In one exemplary embodiment, as shown in FIG. 2, the cutting assembly can include an I-beam compression member 28 that travels through slots formed in each jaw to pull the jaws into a parallel orientation and to compress tissue therebetween. The compression member 28 can include a cutting element (not shown) positioned at the distal end 28d thereof and formed on a connecting portion 30c of the compression member 28. In some embodiments, the cutting element can be integrally formed with the distal end 28d of the compression member 28. The cutting element can have a sharp or serrated edge configured to transect the tissue. In some embodiments, the cutting element can be recessed relative to distal ends of upper and lower flanges 30a, 30b of the I-beam compression member 28 so that compression occurs prior to transecting or cutting of the tissue. In another embodiment, the cutting element can include a shaft having a knife blade that is not attached to a compression member such that the cutting assembly can advance and retract relative to the jaws without applying compression to the tissue.

Figure 3:
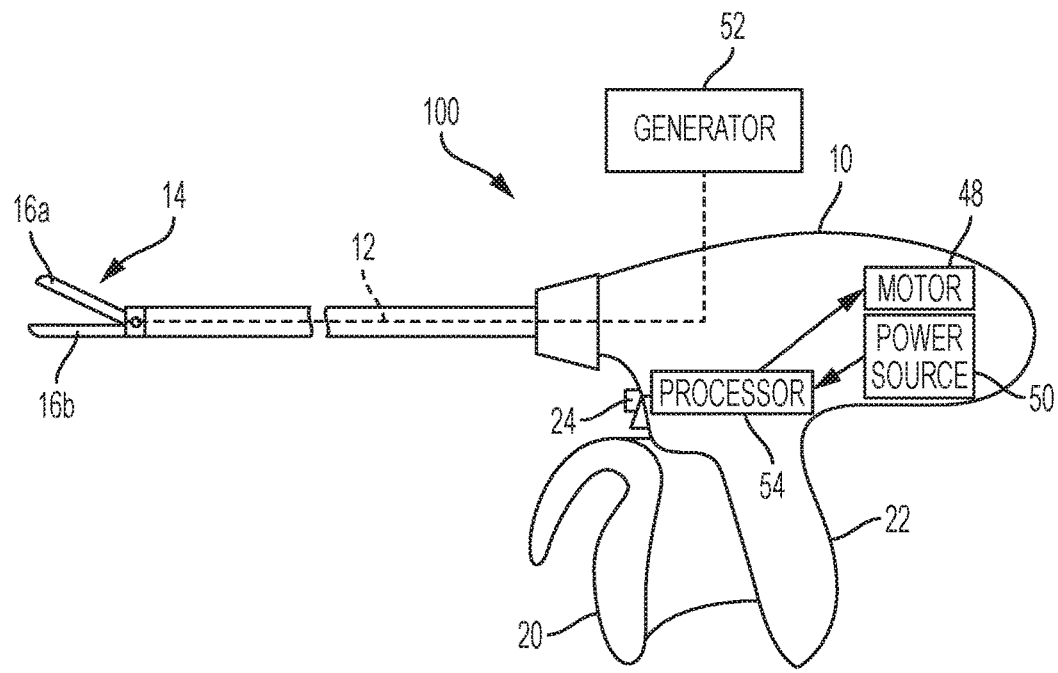
FIG. 3 is another side view illustration of the powered surgical device of FIG. 1, schematically illustrating various components in the handle of the device.

As shown in FIG. 3, the handle portion 10 of the surgical device 100 can include components for operating the device, such as a motor 48, a power source 50, a generator 52, and a processor 54, as well as various sensors (not shown). The device 100 can also include various components for delivering energy, such as radiofrequency or ultrasound energy, to tissue, and these components can be disposed at various locations in the device 100, such as in the proximal handle portion 10 and/or in the jaws 16a, 16b. The firing actuator 24 can be coupled to the processor 54, and the processor 54 can be coupled to the motor 58, the power source 50, and/or the generator 52 (as well as any sensors provided). Firing the actuator 24 sends a signal to the processor 54, which can cause the power source 50 to provide power to the motor 48 through the processor 54. The motor 48 can drive the cutting assembly, and the processor 54 can control a speed and a direction of the motor, which in turn alters a speed and a direction of the cutting assembly.

The generator 52 can be a separate unit that is electrically connected to the surgical device 100 to decrease the size and weight of the surgical device 100, and it can be operatively coupled to an actuator on the surgical device so that the device is configured to apply energy to tissue engaged by the end effector when the actuator is activated. The generator can be operably coupled to the firing actuator 24 or the generator can be coupled to a second actuator. The generator can be any suitable generator known in the art, such as an RF generator or an ultrasound generator. A lumen (not shown) of the shaft portion 12 can carry electrical leads or wires that can deliver electrical energy to components of the end effector 14. The generator 52 can be coupled to the power source 50, such as a battery disposed in the proximal handle portion 10 or it can be coupled to an external power source, such as an electrical outlet.

Figure 4:
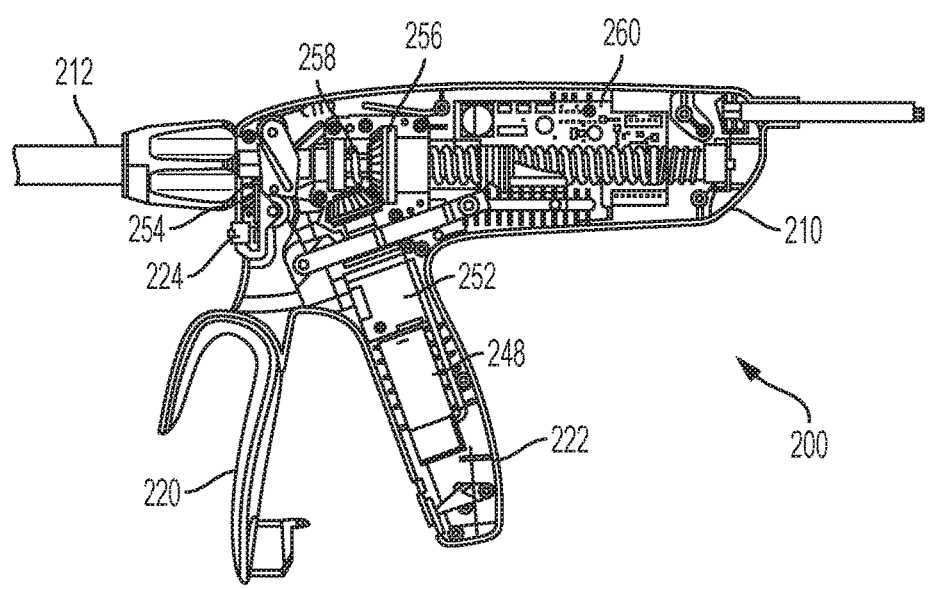
FIG. 4 is a side cutaway view of another embodiment of a powered surgical device.

FIG. 4 illustrates one exemplary configuration of a surgical device 200 having components for operating the device. The surgical device 200 can generally be configured and used similar to the surgical device 100 of FIGS. 1-3. As seen in FIG. 4, the surgical device 200 has a shaft portion 212, and a proximal handle portion 210 including a closure grip 220 and a stationary grip 222. The surgical device 200 has a firing actuator 224 that is configured to advance distally and/or retract proximally a cutting assembly through an end effector (not shown) positioned on a distal end of the shaft portion 212. The firing actuator 224 is a button that can be depressed by a user. The firing actuator 224 is coupled to and in communication with a processor 260, which can include a circuit board and/or a controller. The processor 260 can in turn be in communication with a motor 248, a power source such as a battery, and/or a generator. The motor 248 is disposed in the proximal handle portion 210, and it can be operatively coupled to a gear box 252, which is operably coupled to a motor bevel gear 254. The motor bevel gear 254 is operably coupled in turn to a drive bevel gear 256, which is operably coupled to a drive shaft 258. Activation of the firing actuator 224 can thus provide a signal to the processor 260. The processor 260 can cause power to be delivered from the power source to the motor 248, which rotates the gear box 252. The gear box 252 causes the motor bevel gear 254 to rotate, which engages with and rotates the drive bevel gear 256, which drives the drive shaft 258 distally or proximally. Upon rotation of the drive bevel gear 256, the drive shaft 258 can be driven distally or proximally through known means, such as a thread along the drive shaft 258. Distal movement of the drive shaft 258 advances the cutting assembly distally through an end effector. Proximal movement of the drive shaft 258 retracts the cutting assembly proximally from the end effector. A person skilled in the art will appreciate that the drive shaft can be advanced and retracted using a number of different techniques, such as a rack system, one or more linkages, a ball bearing and nut system, a bevel and spur gear system, etc.

As indicated above, the surgical device 200 has a generator (not shown) that is operatively coupled to an actuator on the surgical device 200 so that the device 200 is configured to apply energy to tissue engaged by the end effector when the actuator is activated. The generator can be operably coupled to the firing actuator 224 or the generator can be coupled to a second actuator. The generator can be any suitable generator known in the art, such as an RF generator or an ultrasound generator. A lumen (not shown) of the shaft portion 212 can carry electrical leads or wires that can deliver electrical energy to components of the end effector.

Under normal operation of a surgical device as described above, power can be supplied from a power source, e.g., the battery, through a processor to a motor, resulting in distal or proximal movement of a cutting assembly through an end effector positioned on a distal end of the surgical device. In certain instances, the surgical device may fail to successfully complete a cutting stroke, for example if the device jams during cutting because of thick tissue or if a power failure occurs. Removing the surgical device from a patient before retracting the cutting assembly may cause significant harm to the patient, though. If the surgical device malfunctions during a firing stroke, i.e., prior to full advancement and full retraction of the cutting assembly, a surgeon may be required to retract the cutting assembly from the jaws of the end effector. Accordingly, a bailout mechanism is provided that can allow retraction of the cutting assembly in the event of a malfunction.

In general, a surgical device can be provided with a handle and an elongate shaft extending distally therefrom. The elongate shaft can have an end effector at a distal end thereof, which can have first and second jaws configured to engage tissue therebetween. A cutting assembly can be configured to move relative to the first and second jaws so as to cut tissue engaged between the first and second jaws. The cutting assembly can be moved distally and proximally by a drive shaft extending from the handle along or through the elongate shaft and being coupled to the cutting assembly. The drive shaft can have a motorized gear assembly coupled to the drive shaft that is configured to cause movement of the drive shaft. The drive shaft can be movable between a first position in which the drive shaft is engaged with the motorized gear assembly such that actuation of the motorized gear assembly drives the drive shaft proximally and distally, and a second position (i.e. a bailout mode) in which the drive shaft is disengaged from the motorized gear assembly. The drive shaft can thus be manually retracted to withdraw proximally from the jaws of the end effector. The first and second jaws can then open to release tissue engaged between, and a surgeon can subsequently withdraw the surgical device from a patient. The second bailout position of the drive shaft may allow a surgeon to rapidly remove the surgical device during any emergency situation, for example if normal operation of the device malfunctions, while minimizing any harm to the patient. Manual bailout of the cutting assembly in the form of disengaging the drive shaft may also be fast and less prone to electronic error than other mechanisms, ensuring a safe retraction during a potentially high-stress situation in which the surgeon is attempting to monitor the patient and safely remove the device at the same time.

FIGS. 5-7 illustrate one embodiment of a surgical device 300 having a bailout mechanism. Surgical device 300 is similar to the aforementioned devices and has a shaft portion (not shown) and a proximal handle portion 310 including a closure grip (not shown) and a stationary grip 322. The surgical device 300 has a firing actuator (not shown) that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor (not shown) within the proximal handle portion 310. The processor is connected to and in communication with a motor 348 and a power source (not shown) such as a battery. The motor 348 is operably coupled to a gear box 352 and is disposed in the proximal handle portion 310. The motor 348 and the gear box 352 can be operatively coupled to a motor bevel gear 354 that is operably coupled to a drive bevel gear 356, which in turn is operably coupled to a drive shaft 358.

In this embodiment, the drive shaft 358 is coupled to the drive bevel gear 356 by a lead screw nut 332 that is fixed axially, but that is coupled to the drive bevel gear 356 by a tube 334. As a result, the lead screw nut 332 will rotate with the drive bevel gear 356. The lead screw nut 332 is internally threaded and is engaged with threads formed on the drive shaft 358. As a result, when the lead screw nut 332 rotates, the threads cause axial translation of the drive shaft 358. The lead screw nut 332 is coupled to the tube 334 by a bailout mechanism 330 that includes a spring band 336 and a plurality of balls 338. The spring band 336 is configured to apply inwardly directed compressive force to the balls 338 to force the balls 338 into openings 344 formed in the tube 334. The balls 338 extend through the openings 344 far enough to engage with engagement points 342, such as detents and/or apertures, in the lead screw nut 332, as can be seen in FIG. 6. The bailout mechanism 330 also includes a cone wedge 340 that is disposed in the proximal handle portion 310 just proximal to the lead screw nut 332, and that is movable axially in a distal direction towards the drive bevel gear 356. The cone wedge 340 has a tapered leading distal edge 340d that is configured to force the balls 338 radially outward and out of the engagement points 342 as the cone wedge 340 is moved distally.

When the device 300 experiences normal operation and the drive shaft 358 is in a first position, the spring band 336 compresses the balls 338 into the engagement points 342 on the lead screw nut 332, fixedly coupling the lead screw nut 332 to the tube 334. Actuation of the firing actuator sends a signal to the processor. The processor provides power to the motor 348 from the power source. The motor 348 drives the gear box 352, which rotationally drives the motor bevel gear 354, in turn rotationally driving the drive bevel gear 356 via the tube 334. As the drive bevel gear 356 rotates, the tube 334 rotates with the drive bevel gear 356. The tube 334 rotates in a fixed axial position, the internal threads on the lead screw nut 332 threadably advance the drive shaft 358. The drive shaft 358 fully advances distally, and then the motor reverses direction in response to instructions from the processer to cause the drive shaft 358 to retract proximally and thereby fully retract the cutting assembly from the jaws, representing one full cutting stroke.

When the drive shaft 358 needs to be moved to a second position to allow bailout of the cutting assembly, the cone wedge 340 is advanced distally. The leading distal edge 340d of the cone wedge 340 extends between the balls 338 and the lead screw nut 332, and upon overcoming the spring bias of the spring band 336, forces the balls 338 radially outward to disengage the balls 338 from the engagement points 342 of the lead screw nut 332. The lead screw nut 332 is thus decoupled from the tube 334 and no longer rotates with the tube 334 and the drive bevel gear 356. The lead screw nut 332 and the drive shaft 358 are thus freed to move axially within the tube 334, and the drive shaft 358 is disengaged from the drive bevel gear's rotation. Any further rotation of the drive bevel gear 356 will not affect the drive shaft 358, preventing any accidental activation of the motor 348 from driving the drive shaft 358. The drive shaft 358 can then be manually retracted relative to the elongate shaft, thereby retracting the cutting assembly from the jaws.

The cone wedge 340 can be advanced and the drive shaft 358 can be withdrawn in a variety of ways. For example, an interior of the proximal handle portion 310 can be accessible through an access panel to allow manual advancement of the cone wedge 340 and withdrawal of the drive shaft 358. Alternatively, handles or an actuator can extend externally from the proximal handle portion 310 and can be coupled to the cone wedge 340 and/or the drive shaft 358, allowing manipulation of the cone wedge 340 and/or the drive shaft 358 without opening the proximal handle portion 310. As another example, the bailout mechanism 330 can be controlled through software and electrically coupled to the processor.

In one embodiment, the drive shaft can be limited to manual proximal movement to allow only withdrawal of the cutting assembly. Other embodiments can include mechanisms to prevent over-retraction, such as a stopper positioned in the path of retraction in the proximal handle portion to contact the cutting assembly and prevent further retraction. In some variations, engagement between the balls and the lead screw nut can serve as a torque-limiting clutch during normal operation to ensure that too much torque is not applied to the surgical device. Splines can be provided in some embodiments on the tube and the lead screw nut to ensure that no rotational slippage occurs between the tube and the lead screw nut. The lead screw nut can be significantly shorter than the drive shaft to save space within the surgical device. In other embodiments, the drive shaft can be freely manually movable in both the proximal and distal directions.

The surgical device 300 can be reused and returned to normal operation by retracting the cone wedge 340, causing the spring band 336 to recompress the balls 338 into the engagement points 342 on the lead screw nut 332 and reengage the lead screw nut 332 with the tube 334. Other variations can prevent the surgical device from being reused, effectively disabling the device, to prevent a malfunctioning surgical device from being used in other operations. For example, the cone wedge can be configured to permanently force the balls out of alignment with the engagement points, by for instance adding tabs on the leading edge of the cone wedge that engage with the tube such that the tabs prevent retraction of the cone wedge.

Figure 8:
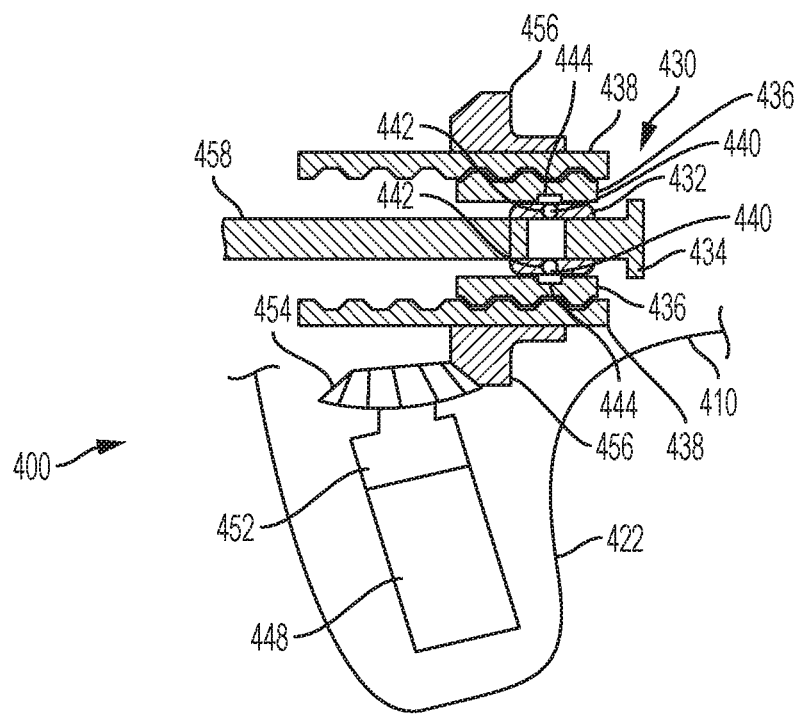
FIG. 8 is a partial side cross-sectional view of another embodiment of a powered surgical device.

FIG. 8 illustrates another embodiment of a surgical device 400 having a bailout mechanism. Surgical device 400 is similar to the above embodiments and has a shaft portion (not shown) and a proximal handle portion 410 including a closure grip (not shown) and a stationary grip 422. The surgical device 400 has a firing actuator (not shown) that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor (not shown) within the proximal handle portion 410. The processor is connected to and in communication with a motor 448 and a power source (not shown) such as a battery. The motor 448 is operably coupled to a gear box 452 and is disposed in the proximal handle portion 410. The motor 448 and the gear box 452 can be operatively coupled to a motor bevel gear 454 that is operably coupled to a drive bevel gear 456, which in turn is operably coupled to a drive shaft 458.

In this embodiment, the drive shaft 458 is coupled to the drive bevel gear 456 by a bailout mechanism 430. The bailout mechanism 430 includes a ball detent coupler 432 that is disposed around and coupled to the drive shaft 458. The ball detent coupler 432 is releasably coupled to a male threaded nut 436 by engagement of a plurality of balls 440. The balls 440 are positioned in openings and/or apertures 442 in the ball detent coupler 432 and engage openings and/or detents 444 in the male threaded nut 436. The male threaded nut 436 is engaged to a female threaded tube 438 that is coupled to the drive bevel gear 456. The female threaded tube 438 is configured to rotate with rotation of the drive bevel gear 456. Rotation of the female threaded tube 438 drives the male threaded nut 436 distally and proximally along the female threaded tube 438 due to the threaded engagement between the female threaded tube 438 and the male threaded nut 436, and due to the male threaded nut 436 being fixed rotationally such that it does not rotate and instead only translates axially. A coupling pin 434 is configured to be inserted into a rear cavity of the ball detent coupler 432, and the coupling pin 434 engages with and forces the balls 440 radially outward into engagement with the detents 444 in the male threaded nut 436.

When the device 400 experiences normal operation and the drive shaft 458 is in a first position (not shown), the coupling pin 434 is inserted into the rear cavity of the ball detent coupler 432. The coupling pin 434 engages with and forces the balls 440 radially outward so that the balls 440 engage the detents 444 in the male threaded nut 436. Engagement of the balls 440 in the detents 444 cause the drive shaft 458 to be fixedly coupled to the male threaded nut 436. Actuation of the firing actuator sends a signal to the processor. The processor provides power to the motor 448 from the power source. The motor 448 drives the gear box 452, which drives the motor bevel gear 454, in turn driving the drive bevel gear 456. As the drive bevel gear 456 rotates, the female threaded tube 438 rotates in a fixed axial position with the drive bevel gear 456. Rotation of the female threaded tube 438 drives the male threaded nut 436 in a proximal or distal direction. Because the male threaded nut 436 is coupled to the drive shaft 458 through the ball detent coupler 432, the coupling pin 434, and the balls 440, proximal or distal movement of the male threaded nut 436 causes proximal or distal movement of the drive shaft 458. The processor causes the motor to fully advance the drive shaft 458 distally and then fully retract the drive shaft 458 proximally, which in turn moves the cutting assembly distally and proximally, representing one full cutting stroke.

When the drive shaft 458 needs to be moved to a second position to allow bailout of the cutting assembly, the coupling pin 434 is moved proximally. Proximal movement of the coupling pin 434 allows the balls 440 to fall out of engagement with the detents 444 on the male threaded nut 436, decoupling the ball detent coupler 432 from the male threaded nut 436. The ball detent coupler 432 will thus no longer move proximally and distally with the male threaded nut 436 as the drive bevel 456 and the female threaded tube 438 rotate. Because the drive shaft 458 is coupled to the ball detent coupler 432, the drive shaft 458 will likewise be free to be manually moved, and any further rotation of the drive bevel gear 456 will not affect the drive shaft 458, preventing any accidental activation of the motor 448 from driving the drive shaft 458. The drive shaft 458 can then be manually withdrawn relative to the elongate shaft, retracting the cutting assembly during the same movement.

The coupling pin 434 and the drive shaft 458 can be withdrawn in a variety of ways. For example, an interior of the proximal handle portion 410 can be accessible through an access panel to allow manual proximal movement of the coupling pin 434 and withdrawal of the drive shaft 458. Alternatively, handles or one or more actuators can extend externally from the proximal handle portion 410 and can be coupled to the coupling pin 434 and/or the drive shaft 458, allowing manipulation of the coupling pin 434 and/or the drive shaft 458 without opening the proximal handle portion 410. As another example, the bailout mechanism 430 can be controlled through software and electrically coupled to the processor.

In one embodiment, the drive shaft can be limited to manual proximal movement to allow only withdrawal of the cutting assembly. Other embodiments can include mechanisms to prevent over-retraction, such as a stopper positioned in the path of retraction in the proximal handle portion to contact the cutting assembly and prevent further retraction. In other embodiments, the drive shaft can be freely manually movable in both the proximal and distal directions.

Upon removal of the coupling pin 434, the balls 440 fall out of engagement through normal movement of the device 400. Other variations can cause the balls to move inward, for example by causing the balls to be spring biased inward due to a spring band around the balls. The surgical device 400 cannot be reused and returned to normal operation after the coupling pin 434 has been removed. Other variations can allow the surgical device to be reused. For example, upon proximal movement of the coupling pin, the balls can be configured to disengage from the male threaded nut while remaining in the openings in the ball detent coupler, allowing the coupling pin to be reinserted to move the balls radially outward causing reengagement between the ball detent coupler and the male threaded nut.

Figure 9:
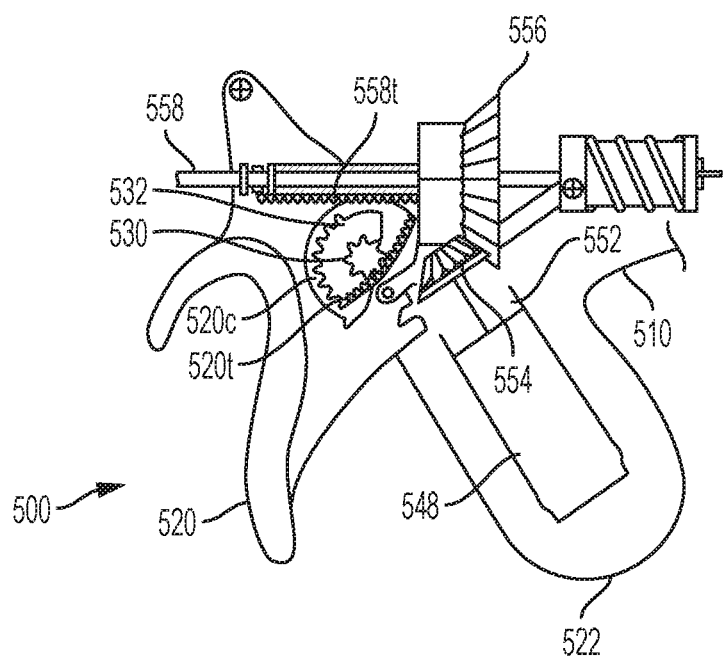
FIG. 9 partial side cutaway view of another embodiment of a powered surgical device.
Figure 10:
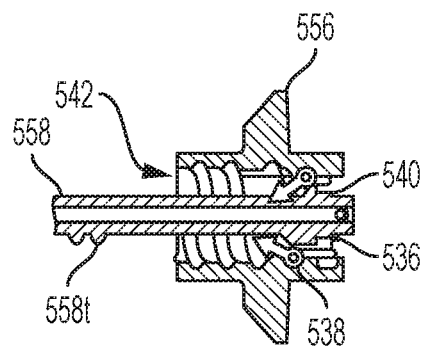
FIG. 10 is a cross-sectional view of the bevel gear and the drive shaft of FIG. 9.

FIGS. 9-10 illustrate another embodiment of a surgical device 500 having a bailout mechanism. Surgical device 500 is similar to the above embodiments and has a shaft portion (not shown) and a proximal handle portion 510 including a closure grip 520 and a stationary grip 522. The surgical device 500 has a firing actuator (not shown) that can be configured to advance distally and/or retract proximally a cutting assembly through an end effector (not shown) positioned on a distal end of the shaft portion. The closure grip 520 is effective to move jaws of the end effector between open and closed positions. The firing actuator is connected to and in communication with a processor (not shown) within the proximal handle portion 510. The processor is connected to and in communication with a motor 548 and a power source (not shown) such as a battery. The motor 548 is operably coupled to a gear box 552 and is disposed in the proximal handle portion 510. The motor 548 and the gear box 552 can be operatively coupled to a motor bevel gear 554 that is operably coupled to a drive bevel gear 556, which in turn is operably coupled to a drive shaft 558.

In this embodiment, the drive shaft 558 is coupled to the drive bevel gear 556 by a plurality of balls 538 seated within threading in an interior threaded portion 542 of the drive bevel gear 556, as seen in FIG. 10. The drive bevel gear 556 is configured to rotate, causing the balls 538 to move within the thread tracks and thereby advance distally or proximally. The balls 538 engage ball engagement tabs 540 on the drive shaft 558 to thereby drive the drive shaft 558 distally or proximally therewith. A spring 536 is positioned proximal to the ball engagement tabs 540 and biases the ball engagement tabs 540 and the drive shaft 558 in a distal direction towards the drive bevel gear 556 to keep the balls 538 engaged with the ball engagement tabs 540. As shown in FIG. 9 and as can be used during a bailout mode, a cavity 520c is formed in the closure grip 520 and has teeth 520t formed along a back side of the cavity 520c. A grip gear 530 engages the teeth 520t in the cavity 520c, and the grip gear 530 is coupled to and causes rotation of a shaft gear 532. The shaft gear 532 is configured to engage teeth 558t on the drive shaft 558.

When the device 500 experiences normal operation and the drive shaft 558 is in a first position, the grip gear 530 is rotated by the teeth 520t in the cavity 520c of the closure grip 520 as the closure grip 520 is pulled towards the stationary grip 522. The grip gear in turn 530 rotates the shaft gear 532. Under normal operations the shaft gear 532 does not engage the teeth 558t on the drive shaft 558 because teeth on the shaft gear 532 are only formed on part of the shaft gear 532, as can be seen in FIG. 9. Thus under a normal range of rotation of the shaft gear 532, there are no corresponding teeth on the shaft gear 532 to engage with teeth 558t on the drive shaft 558. Actuation of the firing actuator sends a signal to the processor. The processor provides power to the motor 548 from the power source. The motor 548 drives the gear box 552, which drives the motor bevel gear 554, in turn driving the drive bevel gear 556. As the drive bevel gear 556 rotates, the threaded portion 542 rotates and drives the balls 538 distally or proximally along threading in the threaded portion 542. The balls in turn drive the drive shaft 558 distally or proximally by engaging the ball engagement tabs 540 of the drive shaft 558. The drive shaft 558 fully advances distally and then fully retracts proximally the cutting assembly, representing one full cutting stroke.

When the drive shaft 558 needs to be moved to a second position to allow bailout of the cutting assembly, the closure grip 520 can be pushed distally away from the stationary grip 522 to a degree beyond a normal range of movement for the closure grip. The grip gear 530 is rotated by the teeth 520t in the cavity 520c of the closure grip 520 as the closure grip 520 is pushed beyond the normal range away from the stationary grip 522. The grip gear 530 causes rotation of the shaft gear 532, and the over-movement of the closure grip 520 causes the teeth on the shaft gear 532 to engage with the teeth 558t on the drive shaft 558. When the teeth 558t on the drive shaft 558 are engaged by the shaft gear 532, continued over-movement of the closure grip 520 and rotation of the shaft gear 532 causes the drive shaft to be forced proximally, compressing the spring 536. The ball engagement tabs 540 on the drive shaft 558 are likewise moved proximally. As can be seen by the arrows in FIG. 10, proximal movement of the ball engagement tabs 540 relative to the balls 538 causes the balls 538 to fall out of alignment with the tabs 540, allowing the balls to move radially inward and to thus be disengaged from the threaded portion 542. Since the balls 538 and the drive shaft 558 are no longer engaged with the threaded portion 542, the drive shaft 558 is disengaged from the drive bevel gear 556. Any further rotation of the drive bevel gear 556 will not affect the drive shaft 558, preventing any accidental activation of the motor 548 from driving the drive shaft 558. The drive shaft 558 can then be manually withdrawn from the elongate shaft, retracting the cutting assembly during the same movement.

The drive shaft 558 can be withdrawn in a variety of ways. For example, the closure grip 520 can be continued to be pushed beyond the normal range of movement after the balls 538 have dropped out of alignment, which will continue to retract the drive shaft 558 and the cutting assembly. In other variations, an interior of the proximal handle portion can be accessible through an access panel to allow manual withdrawal of the drive shaft. Alternatively, a handle can extend externally from the proximal handle portion that is coupled to the drive shaft, allowing manipulation of the drive shaft without opening the proximal handle portion.

In one embodiment, the drive shaft can be limited to manual proximal movement to allow only withdrawal of the cutting assembly. Other embodiments can include mechanisms to prevent over-retraction, such as a stopper positioned in the path of retraction in the proximal handle portion to contact the cutting assembly and prevent further retraction. The surgical device 500 cannot be reused and returned to normal operation after a bailout of the cutting assembly. In other embodiments, the drive shaft can be freely manually movable in both the proximal and distal directions.

Figure 11:
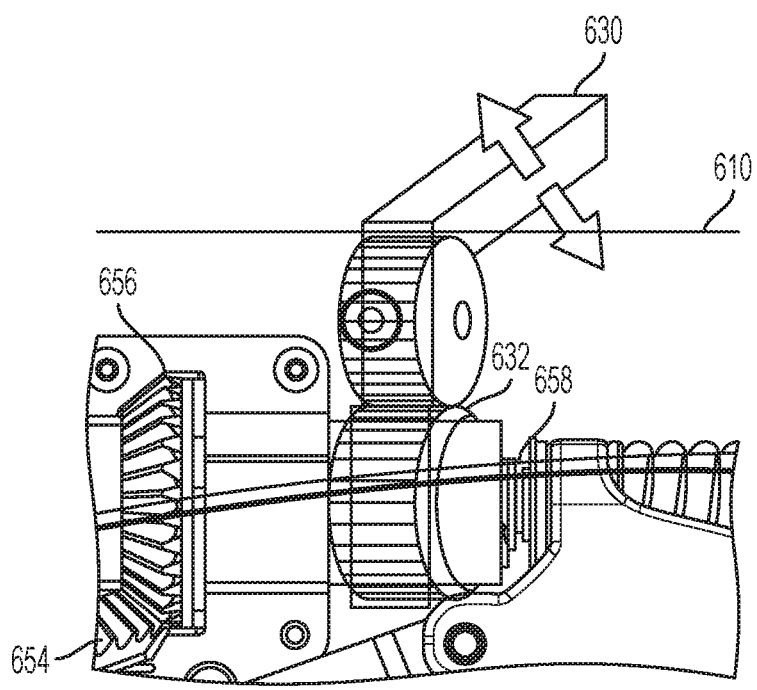
FIG. 11 is a partial side cutaway view of a bailout mechanism to be used with any of FIGS. 5-10.

One embodiment of a mechanism for removing a drive shaft once the drive shaft has been disengaged is shown in FIG. 11. The mechanism can be incorporated into any of the embodiments shown in FIGS. 5-10, and consists of a lever 630 or a ratchet that extends externally through a proximal handle portion 610 of a surgical device. The lever 630 engages with a bailout gear 632 that is coupled to a drive shaft 658. Under normal operations, the drive shaft 658 is driven through operation of a motor and gear box (not shown), a motor bevel gear 654, and a drive bevel gear 656, similar to the surgical devices of FIGS. 1-10. Once the drive shaft 658 has been disengaged from the drive bevel gear 656 using a similar approach to any of those from FIGS. 5-10, the lever 630 is moved back and forth to rotate the bailout gear 632. Rotation of the bailout gear 632 drives proximal movement of the drive shaft 658 to retract the drive shaft 658 and a cutting assembly.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device," incorporated herein by reference in its entirety. It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a handle portion having an elongate shaft extending distally therefrom, the elongate shaft having first and second jaws at a distal end thereof, the jaws being configured to engage tissue therebetween;
   a cutting assembly configured to move relative to the first and second jaws so as to cut tissue engaged between the first and second jaws;
   a drive shaft extending from the handle through the elongate shaft and being coupled to the cutting assembly for moving the cutting assembly relative to the first and second jaws; and
   a motorized gear assembly coupled to the drive shaft and configured to cause movement of the drive shaft;
   wherein the drive shaft is movable between a first position in which the drive shaft is operatively engaged with the motorized gear assembly such that actuation of the motorized gear assembly drives the drive shaft, and a second position in which the drive shaft is operatively disengaged from the motorized gear assembly such that the drive shaft can move independent of the gear assembly, and
   wherein the drive shaft is operatively engaged to the motorized gear assembly by a nut and ball bearing assembly.

2. The device of claim 1, wherein the handle portion includes a lever configured to open and close the jaws.

3. The device of claim 2, wherein the lever includes a plurality of gears engageable with the drive shaft.

4. The device of claim 1, wherein a removable pin biases a plurality of balls to operably couple the drive shaft to the motorized gear assembly, and proximal movement of the pin causes the balls to disengage the drive shaft from the motorized gear assembly.

5. The device of claim 1, wherein a plurality of balls operatively engages the drive shaft to the motorized gear assembly, and a wedge is configured to be moved distally to cause the balls to operatively disengage the drive shaft from the motorized gear assembly.

6. A surgical device, comprising:
   a handle having an elongate body extending distally therefrom and having first and second jaws on a distal end of the elongate body;
   a cutting assembly configured to move relative to the first and second jaws so as to cut tissue engaged between the first and second jaws; and
   a drive shaft extending through an elongate shaft and being coupled to the cutting assembly for moving the cutting assembly relative to the first and second jaws, the drive shaft being operably coupled to a motor by a ball and detent assembly, the ball and detent assembly being releasable to disengage the drive shaft from the motor.

7. The device of claim 6, wherein a cone is distally advanceable along the drive shaft to release the ball and detent assembly.

8. The device of claim 6, wherein the handle includes a lever configured to release the ball and detent assembly to disengage the drive shaft from the motor.

9. The device of claim 8, wherein the lever includes a plurality of gears engageable with the drive shaft.

10. The device of claim 8, wherein the lever overcomes a spring bias to release the ball and detent assembly.

11. The device of claim 6, wherein a removable pin biases the ball and detent assembly to operatively couple the drive shaft to the motor, and proximal movement of the pin causes the ball and detent assembly to operatively disengage the drive shaft from the motor.

12. A surgical device, comprising:
 a handle portion having an elongate shaft extending distally therefrom, the elongate shaft having first and second jaws at a distal end thereof, the jaws being configured to engage tissue therebetween;
 a cutting assembly configured to move relative to the first and second jaws so as to cut tissue engaged between the first and second jaws;
 a drive shaft extending from the handle through the elongate shaft and being coupled to the cutting assembly for moving the cutting assembly relative to the first and second jaws; and
 a motorized gear assembly coupled to the drive shaft and configured to cause movement of the drive shaft;
 wherein the drive shaft is movable between a first position in which the drive shaft is operatively engaged with the motorized gear assembly such that actuation of the motorized gear assembly drives the drive shaft, and a second position in which the drive shaft is operatively disengaged from the motorized gear assembly such that the drive shaft can move independent of the gear assembly, and
 wherein a plurality of balls operatively engages the drive shaft to the motorized gear assembly, and a wedge is configured to be moved distally to cause the balls to operatively disengage the drive shaft from the motorized gear assembly.

13. The device of claim 12, wherein the handle portion includes a lever configured to open and close the jaws, and the lever includes a plurality of gears engageable with the drive shaft.

14. The device of claim 12, wherein the handle includes a lever configured to move the wedge to disengage the drive shaft from the motorized gear assembly.

* * * * *